United States Patent [19]

Majeed et al.

[11] Patent Number: 5,861,415
[45] Date of Patent: Jan. 19, 1999

[54] BIOPROTECTANT COMPOSITION, METHOD OF USE AND EXTRACTION PROCESS OF CURCUMINOIDS

[75] Inventors: Muhammed Majeed; Vladimir Badmaev, both of Piscataway, N.J.; R. Rajendran, Bangalore, India

[73] Assignee: Sami Chemicals & Extracts, Ltd., Bangalore, India

[21] Appl. No.: 945,311

[22] PCT Filed: Jul. 12, 1996

[86] PCT No.: PCT/US96/11431

§ 371 Date: Oct. 27, 1997

§ 102(e) Date: Oct. 27, 1997

[87] PCT Pub. No.: WO97/03674

PCT Pub. Date: Feb. 6, 1997

Related U.S. Application Data

[60] Provisional application No. 60/001,161, Jul. 14, 1995.

[51] Int. Cl.$^6$ .................. A61K 31/445; A61K 31/28; A61K 31/30; A61K 31/075
[52] U.S. Cl. ............. 514/321; 424/195.1; 514/492; 514/499; 514/505; 514/720; 514/733; 568/324; 568/325; 568/334
[58] Field of Search ............ 424/195.1; 514/321, 514/492, 499, 505, 720, 733; 568/324, 325, 334

[56] References Cited

U.S. PATENT DOCUMENTS

| | | | |
|---|---|---|---|
| 4,263,333 | 4/1981 | Maing et al. | 426/540 |
| 4,719,111 | 1/1988 | Wilson | 424/195.1 |
| 5,108,750 | 4/1992 | Liu | 424/195.1 |
| 5,120,538 | 6/1992 | Oei | 424/195.1 |
| 5,266,344 | 11/1993 | Mimura et al. | 426/546 |
| 5,401,504 | 3/1995 | Das et al. | 424/195.1 |
| 5,401,777 | 3/1995 | Ammon et al. | 514/731 |

OTHER PUBLICATIONS

Biological Abstacts, vol. 100, Issue 12, pp. 2493–2497, "Effects of Curcumin . . . ", 1995.
Chem. Pharm. Bull. vol. 33, No. 4, pp. 1725–1728, "Natural Antioxidants . . . ", 1985.
Journal of Ethno–Pharmacology, vol. 38, pp. 113–119, "Mechanism of Antiinflammatory Actions of Curcumine and Boswellic Acids", 1993.

*Primary Examiner*—Frederick Krass
*Attorney, Agent, or Firm*—Nikaido Marmelstein Murray & Oram, LLP

[57] ABSTRACT

Curcuminoids have been found to have anti-oxidant, anti-inflammatory, antibacterial, antifungal, antiparasitic, antimutagen, anticancer and detox properties. The present invention is directed to compositions containing three curcuminoids, i.e. curcumin, demethoxy curcumin and bis demethoxy curcumin, extracted from roots of tumeric. These compositions have been found to have activity in the anti-oxidant mechanisms of prevention and intervention.

17 Claims, 5 Drawing Sheets

CURCUMIN

BISDEMETHOXY CURCUMIN

DEMETHOXY CURCUMIN

TETRAHYDRO CURCUMIN

BIOPROTECTANT COMPOSITION, METHOD OF USE AND EXTRACTION PROCESS OF CURCUMINOIDS

This is a prov. appln. of Ser. No. 60-001,161, filed Jul. 14, 1995.

I. A novel concept of bioprotectant activity

Curcuma longa (Fam. Zingiberaccae) or Turmeric is one of the oldest herbs in Ayurveda materia medica, and has been used in Ayurveda medicine internally as a stomach, tonic and blood purifier, and topically in the prevention and treatment of skin diseases. The significance of turmeric in medicine has changed considerably since the very recent discovery of the anti-oxidant properties of naturally occurring phenolic compounds. The same ground dried rhizome of *Curcuma longa*, which has been used for centuries as a spice, food preservative and a coloring agent, has been found to be a rich source of phenolic compounds or curcuminoids. There are three main curcuminoids recognized, i.e., curcumin (diferuloylmethane), demethoxy curcumin(p-hydroxycinnamoyl[feruloyl]methane) and bis demethoxy curcumin(p,p-dihydroxydicinnamoylmethane).

Curcuminoids have scientifically documented anti-oxidant, anti-inflammatory, anti-bacterial, anti-fungal, antiparasitic, anti-mutagen, anti-cancer and detox properties. Their potential use in the prevention of cancer and in the treatment of infection with human immunodeficiency virus (HIV) are the subject of intensive laboratory and clinical research. Curcuminoids are recognized for their broad biological activity and safety of use. The biological activity of curcuminoids can best be described by the word "protective".

Curcumin and turmeric have been used as anti-inflammatory drugs for many years. More recently, there has been much interest in possible chemopreventive effects of curcumin. Curcumin inhibits tumor initiation by benxo[a]pyrene and tumor promotion by 12-0-tetradecanoylphorbol-13-acetate (TPA) in female CD-1 mice.

THE BIOLOGICAL ACTIVITIES OF CURCUMIN

| | The biological activity | Inhibition |
|---|---|---|
| 1. | TPA-induced epidermal ornithine decarboxylase activity | ++++ |
| 2. | TPA-induced edema of mouse ear | ++++ |
| 3. | TPA-induced epidermal hyperplasia | ++++ |
| 4. | TPA-induced epidermal DNA synthesis | + |
| 5. | Arachidonic acid-induced edema of mouse ear | +++ |
| 6. | Epidermal lipoxygenase activity | ++++ |
| 7. | Epidermal cyclooxygenase activity | ++++ |
| 8. | TPA-induced skin tumor promotion in previously initiated mice | ++++ |

Co-application of curcumin with TPA inhibits TPA-induced skin inflammation, increased epidermal ornithine decarboxylase activity. Huang et al. have also shown that 2; curcumin in the diet inhibits azoxymethane-induced foci in the colon of CF-1 mice and inhibits duodenal tumorigenesis in C57BL/6J mice previously initiated with N-ethyl-N'-nitro-N-nitrosguanidine.

Many of the anti-inflammatory and chemopreventive properties of curcumin may be related to the antioxidant properties of curcumin. In the present study, the antioxidant properties of curcumin, demethoxycurcumin, bis-demethoxycurcumin and several preparations containing varied proportions of curcumin, demethoxycurcumin, bis-demethoxycurcumin were measured by the Rancimat method.

| $R_1$ | $R_2$ | |
|---|---|---|
| $-OCH_3$ | $-OCH_3$ | Curcumin |
| $-H$ | $-OCH_3$ | Demethoxycurcumin |
| $-H$ | $-H$ | Bisdemethoxycurcumin |

The Rancimat method measures the conductivity changes caused by formation of small fatty acid molecules when the fats and oils are oxidized under elevated temperature and accelerated aeration. The induction times of lard with curcuminoids added were measured. The longer induction times suggest stronger antioxidant activity. All curcuminoids showed excellent antioxidant activity.

Figure 6:
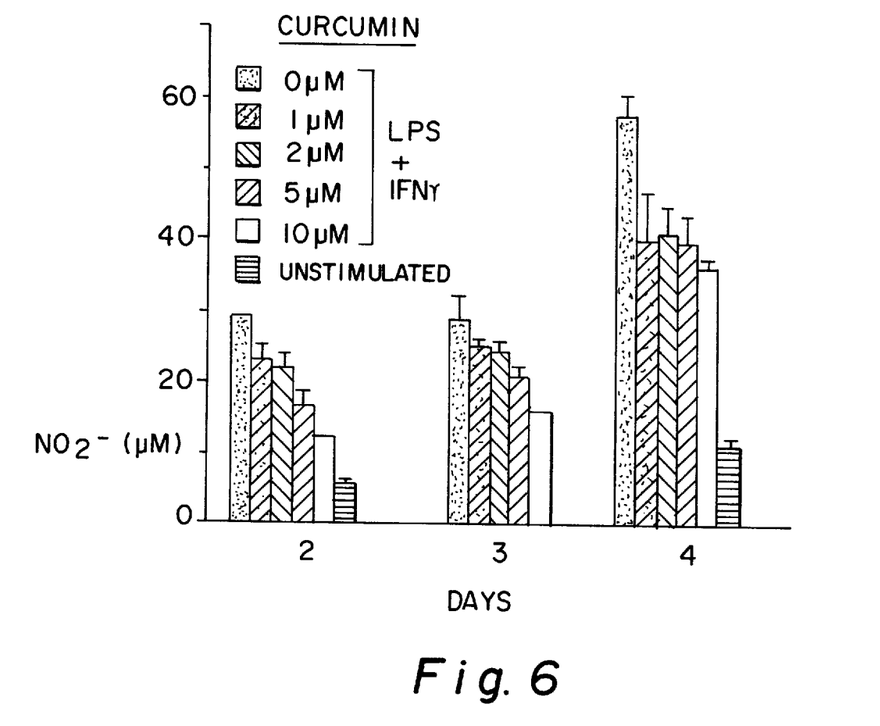
FIG. 6 shows the effect of curcumin on $NO_2^-$ production.

In chronic inflammation, cytokines induce the production of nitric oxide that is converted to DNA damaging and carcinogenic peroxynitrite and nitrite. The effect of curcumin on the generation of peroxynitrite radicals and nitrite was studied. Curcumin inhibited lipopolysaccharide (LPS) and interferon γ (INFγ) induced nitrite production by mouse peritoneal cells by more than 50% at 2.5–10 uM (FIG. 6).

Figure 1:
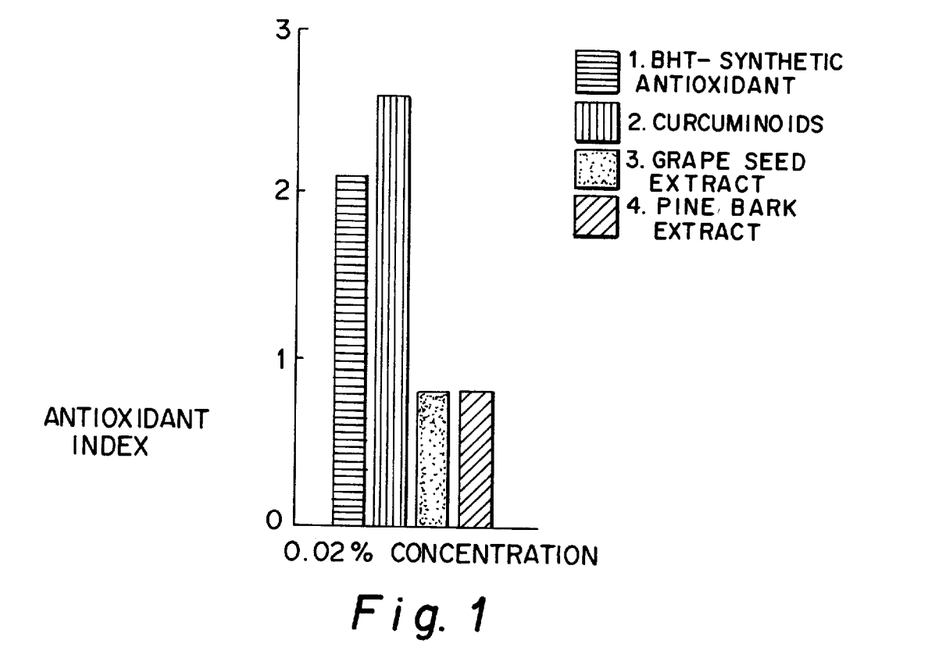
FIG. 1 shows the results of an assay to determine the effectiveness of curcuminoids in the prevention of free radical formation (prevention mode). Free radical formation is measured using the Rancimat method.
Figure 2:
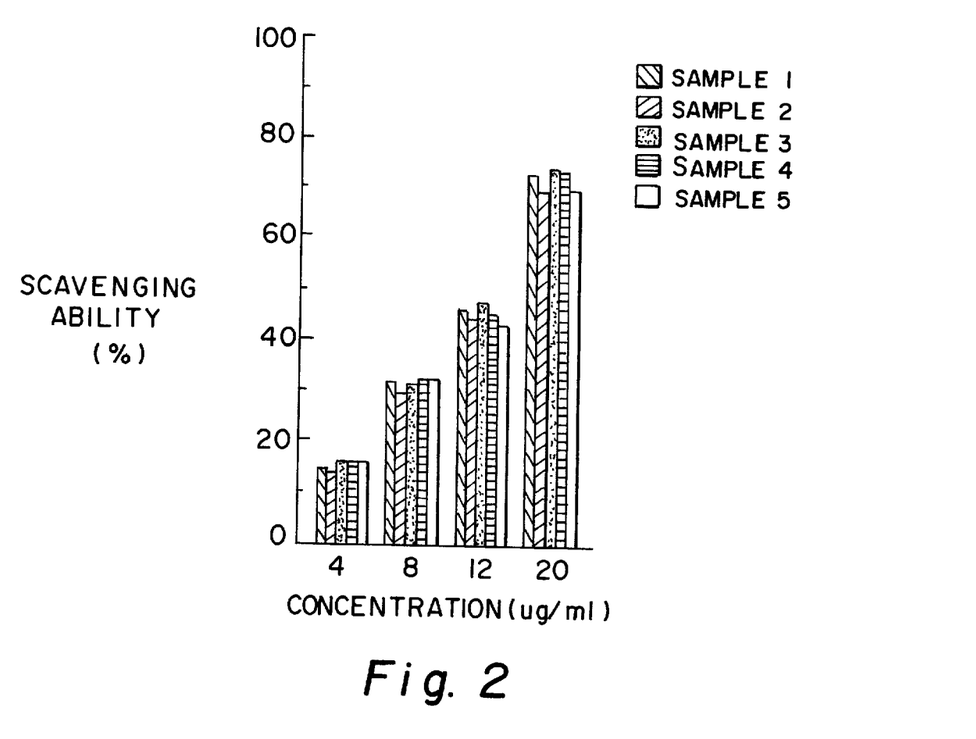
FIG. 2 shows the results of an assay to determine the effectiveness of curcuminoids in scavenging free radicals (intervention mode). The ability to scavenge free radicals is measured using the DPPH Radical Scavenging method.
Figure 3:
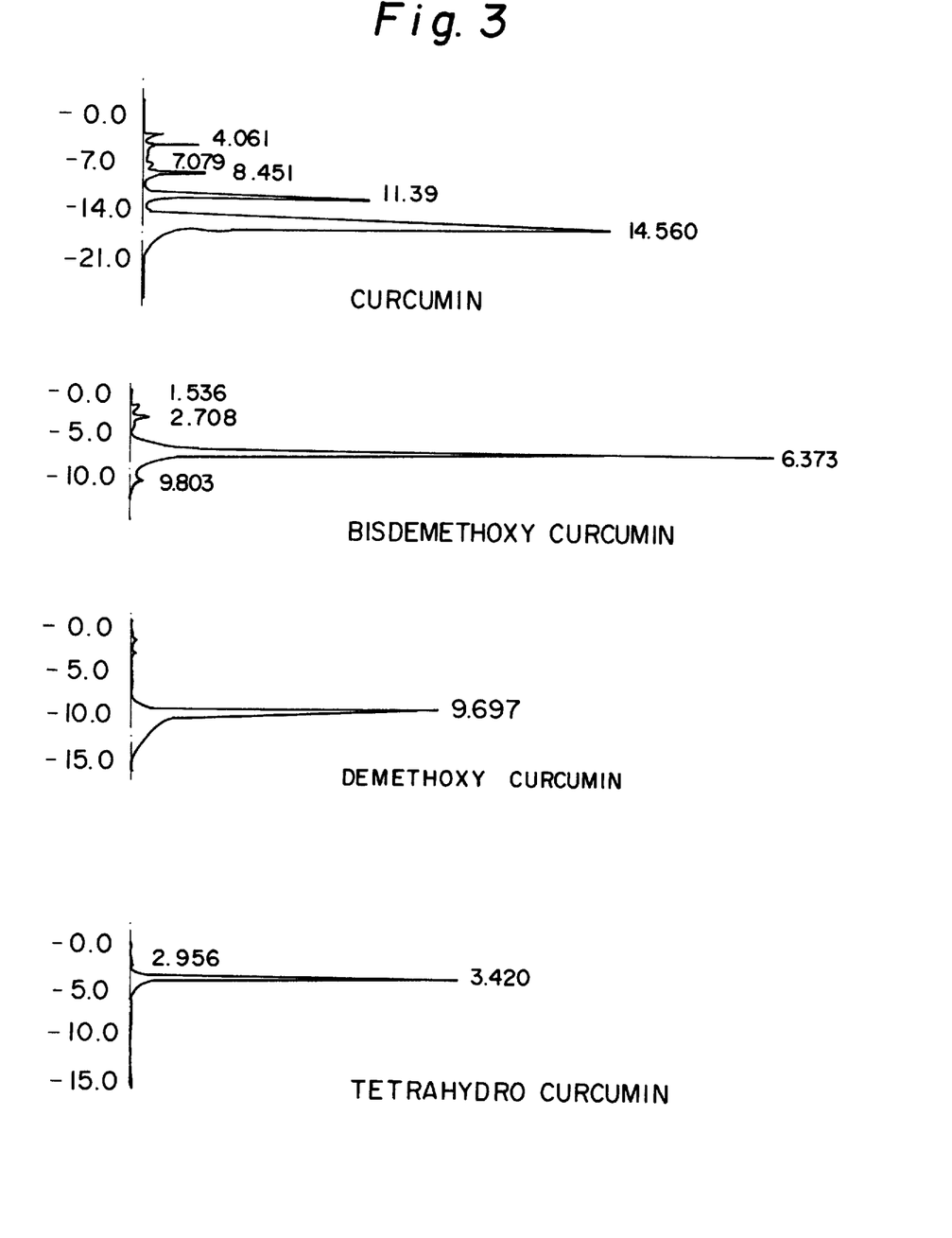
FIG. 3 is an HPLC graph of the main components of the present composition.
Figure 4:
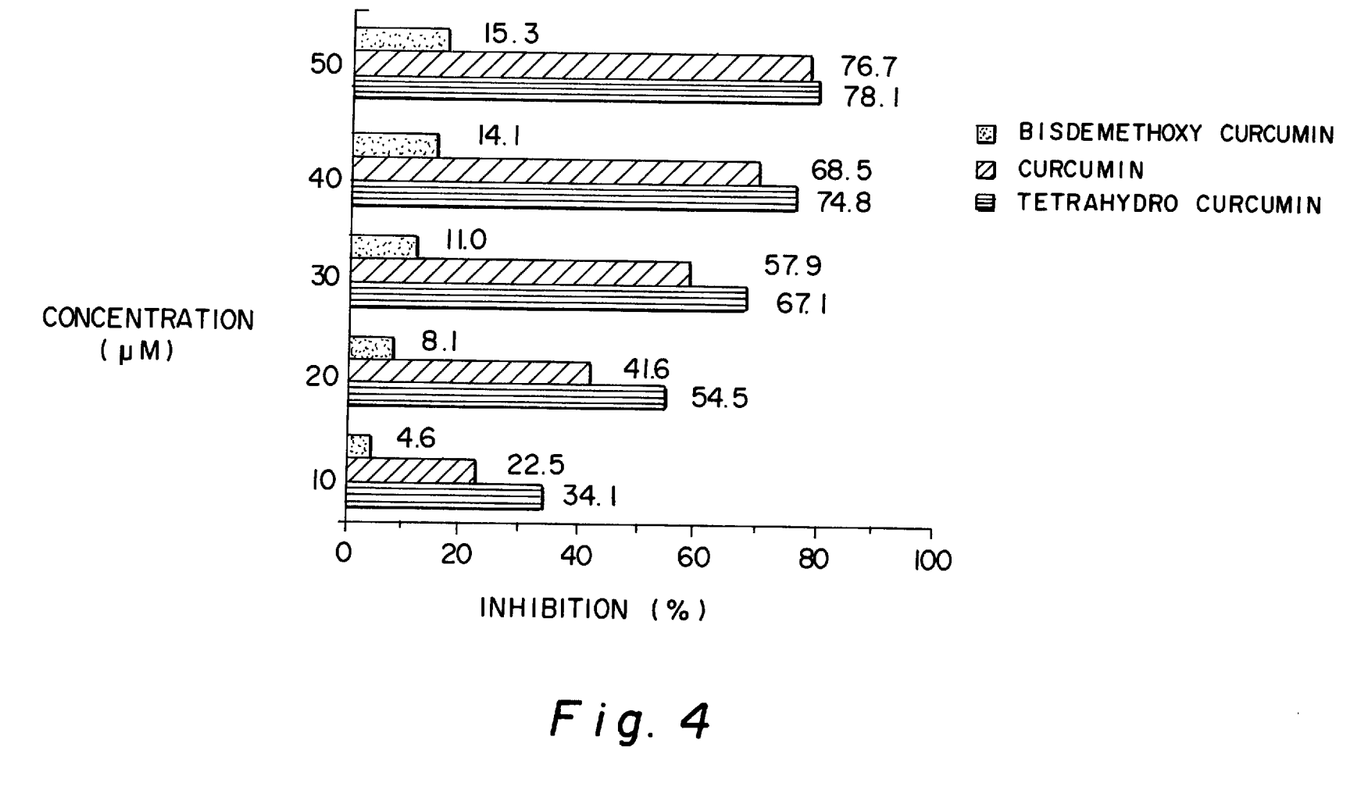
FIG. 4 shows the DPPH radical-scavenging ability of curcumin, tetrahydro curcumin, and bis demethoxy curcumin.
Figure 5:
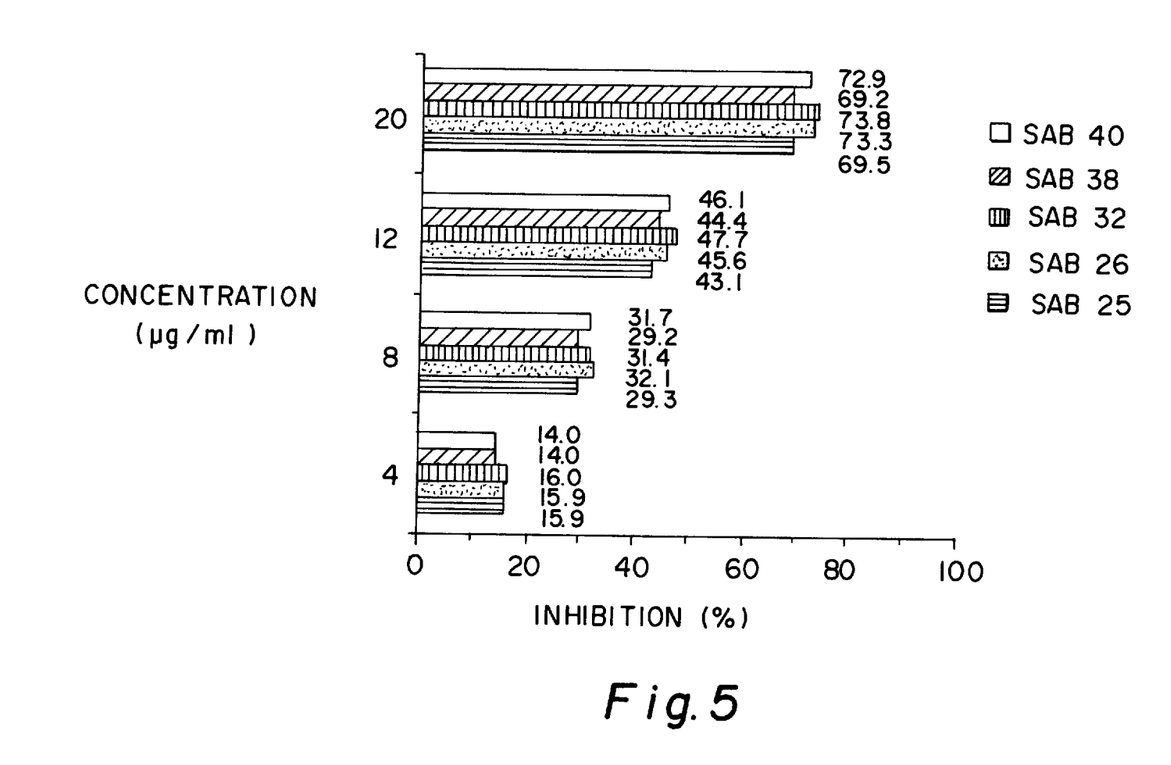
FIG. 5 shows DPPH radical-scavenging ability of mixtures of curcuminoids.

The present invention is directed to a composition containing three curcuminoids, i.e., curcumin, demethoxy curcumin and bis demethoxy curcumin, extracted from roots of turmeric. Curcuminoids possess distinct mechanisms which may explain their "protective" qualities. This protective activity has been defined by testing one of the best known properties of curcuminoids, their anti-oxidant properties. Two distinct modes of anti-oxidant action have been identified in curcuminoids: 1) prevention mode (Table 1) i.e. prevention of the formation of free radicals, and 2) intervention mode (Table 2) i.e. neutralizing action upon the already formed free radicals by the process of free-radical scavenging (FIGS. 4 and 5).

TABLE 1

Prevention mode - the bioprotectant preventive activity of various compounds, as measured by the rancimat method [The rancimat method measures the time needed for inducing oxidative changes in the substrate - the longer the "induction time" the stronger the anti-oxidant properties]. Tested compounds were used in a standard concentration of 0.02%

| SAMPLE | INDUCTION TIME IN HOURS |
|---|---|
| CONTROL | 2.06 |
| BHT (common synthetic phenolic food additive) | 5.05 |
| CURCUMINOID COMPLEX Lot #4226 | 6.05 |
| GRAPE SEED EXTRACT Lot #3034 | 2.13 |
| PINE BARK EXTRACT Lot #1372 | 2.13 |

TABLE 2

Intervention mode - the bioprotectant intervention activity of curcuminoids, measured as DPPH free-radical scavenging ability against a control with "0" ability to scavenge free radicals.

| SAMPLE | CONCENTRATION ug/ml | SCAVENGING ABILITY % |
|---|---|---|
| CURCUMINOID COMPLEX LOT NO. RD/CUR/02 | 4 | 16 |
| CURCUMINOID COMPLEX LOT NO. RD/CUR/02 | 8 | 31.4 |
| CURCUMINOID COMPLEX LOT NO. RD/CUR/02 | 12 | 47.7 |
| CURCUMINOID COMPLEX LOT NO. RD/CUR/02 | 20 | 73.8 |

The composition of the present invention showed significant activity in both anti-oxidant mechanisms studied (prevention and intervention). It should be noted that some other natural anti-oxidants, which have been screened together with curcuminoids, do not offer combined prevention and intervention activity. It has been concluded that the broad biological mechanism of curcuminoids is owed, to a large extent, to the combined mechanisms of prevention and intervention. Prevention and intervention result in the totality of protective qualities. Since curcuminoids may protect the integrity of biological systems by preventing the free-radical assault and by intervening to stop the assault, it is proposed to classify curcuminoids and any similar compound as a "bioprotectant".

The anti-oxidant potential of the composition was evaluated against the individual curcuminoids, i.e., curcumin, demethoxy curcumin, bis demethoxy curcumin, and other natural anti-oxidants like grape seed extract and pine bark extract in vitro. Interestingly, the present composition showed better bioprotectant activities than did the pure compounds as well as the two other natural anti-oxidants.

THE OXIDATIVE INDUCTION TIME AND THE ANTIOXIDANT INDEX OF LARD WITH AND WITHOUT ANTIOXIDANT ADDED

| Sample | Induction time (Hrs) | Antioxidant index |
|---|---|---|
| Control | 2.06 | |
| BHT (Synthetic phenolic) | 5.05 | 2.45 |
| Curcumin 99% Lot #001 | 2.83 | 1.37 |
| BDM Curcumin Lot #06 | 3.48 | 1.69 |
| Curcuminoids Lot #4226 | 6.05 | 2.92 |
| Grape Seed Ex. Lot #3034 | 2.13 | 1.03 |
| Pine Bark Ex. Lot #1372 | 2.13 | 1.03 |

EFFECT OF CURCUMINOID COMPOSITION ON THE ANTIOXIDANT INDEX IN RANCIMAT METHOD

| Sample | Curcumin % | BDM Curcumin % | DM Curcumin % | Anti-oxidant Index |
|---|---|---|---|---|
| SAB 25 | 78.6 | 2.2 | 16.7 | 2.7 |
| SAB 26 | 86.6 | 1.9 | 8.3 | 2.4 |
| SAB 32 | 80.2 | 2.5 | 15.5 | 2.0 |
| SAB 38 | 70.8 | 4.5 | 18.5 | 2.1 |
| SAB 40 | 67.2 | 2.8 | 14.8 | 1.5 |

II. The unique formula for a curcuminoid composition

It has been found that the composition of curcuminoids may affect their bioprotectant activity, since individual components display different bioprotectant potential. For example, curcumin alone does not provide a strong prevention against free-radicals. On the other hand, curcumin shows strong intervention properties in neutralizing the already formed free-radicals. Similarly, a derivative of curcumin, tetrahydrocurcumin (THC), provides excellent intervention in scavenging already formed free-radicals, but is considerably less potent in the prevention of free-radical formation.

As a result of experimentally confirmed differences among various curcuminoid combinations, it has been concluded that only a carefully balanced composition of curcuminoids and derivatives thereof can result in optimal bioprotectant activity.

TABLE 3

Relationship between the composition of curcuminoid mixtures and the anti-oxidant activity as measured with the Rancimat method [The longer the induction time the better the anti-oxidant activity].

| Tested Compound | Curcumin % | DM Curcumin % | BDM Curcumin % | Total Curcumins | Induction Time (hrs.) |
|---|---|---|---|---|---|
| 1. Control | none | none | none | none | 2.00 |
| 2. Complex | 78.6 | 16.7 | 2.2 | 97.5 | 5.55 |
| 3. Complex | 72.0 | 19.4 | 6.7 | 98.4 | 5.32 |
| 4. Complex | 73.9 | 18.1 | 3.4 | 95.4 | 5.28 |
| 5. Complex | 75.1 | 17.8 | 2.3 | 95.2 | 5.20 |
| 6. Complex | 74.2 | 20.6 | 3.1 | 97.9 | 5.08 |
| 7. Complex | 72.9 | 18.9 | 4.7 | 96.5 | 5.07 |
| 8. Complex | 86.6 | 8.3 | 1.9 | 96.8 | 4.80 |

The following observations were made pertaining to the relationship between the different compositions of curcuminoid combinations and their anti-oxidant activity:
- the mixture of curcuminoids is generally a more effective bioprotectant than either of the three components alone;
- the proportion of the individual components occurring in a mixture of curcuminoids is an important factor in determining the bioprotectant properties;
- the total content of curcuminoids is of secondary importance to the bioprotectant properties, primary importance being the presence of the three curcuminoids in the appropriate weight ratio of the individual components;
- the addition of certain derivatives of curcuminoids, e.g., tetrahydrocurcumin; cyclo curcumin; tumerin; curcumin complexed with metals like potassium, zinc, calcium, copper, chromium, vanadium; etc. may increase the bioprotectant activity of curcuminoids.

The following composition of curcuminoids is preferred to afford maximum bioprotectant activity:

1. Curcumin should be present in an amount of no less than 75% and no more than 81% of the total curcuminoids.

2. Demethoxy curcumin should be present in an amount of no less than 15% and no more than 19% of the total curcuminoids.
3. Bis demethoxy curcumin should be present in the amount of no less than 2.2% and no more than 6.5% of the total curcuminoids.
4. Additional ingredients may be present, e.g., tetrahydrocurcumin in an amount ranging from 1% to 5%; curcuminoids complexed with metals like potassium, zinc, copper, chromium, vanadium, calcium, etc. in an amount ranging from 1% to 5%; alkaloid piperine preferably in the form of Bioperine™ (subject of U.S. application Ser. No. 08/393,738 filed on Feb. 24, 1995) in an amount ranging from 0.001% to 1%; cyclo curcumin in an amount ranging from 1% to 5%; and tumerin in an amount ranging from 0.1% to 0.5%.

The following are examples of preferred combinations of curcuminoids and other ingredients:

1. Curcumin 78.6%, demethoxy curcumin 16.7%, bis demethoxy curcumin 2.5%, tetrahydrocurcumin 1%, potassium curcumin 0.5%, Bioperine™ (piperine) 0.5%.
2. Curcumin 80.2%, demethoxy curcumin 15.5%, bis demethoxy curcumin 2.5%, tetrahydrocurcumin 1.8%.
3. Curcumin 75%, demethoxy curcumin 15%, bis demethoxy curcumin 6.5%, tetrahydrocurcumin 2%, Bioperine™ (piperine) 1%.
4. Curcumin 76.8%, demethoxy curcumin 16.1%, bis methoxy curcumin 6.1%.
5. Curcumin 78.6%, demethoxy curcumin 16.7%, bis demethoxy curcumin 2.5%, cyclo curcumin 1%, potassium curcumin 0.5%, Bioperine™ (piperine) 0.5%.
6. Curcumin 78.6%, demethoxy curcumin 16.7%, bis demethoxy curcumin 2.5%, tumerin 0.1%, potassium curcumin 0.5%, Bioperine™ (piperine) 0.5%.
7. Curcumin 80.2%, demethoxy curcumin 15.5%, bis demethoxy curcumin 2.5%, cyclo curcumin 1.8%.
8. Curcumin 75%, demethoxy curcumin 15%, bis demethoxy curcumin 6.5%, cyclo curcumin 2%, Bioperine™ (piperine) 1%.

The present invention is the optimal composition showing both prevention and intervention activity according to the above provided definition of bioprotectants.

III. The unique manufacturing procedure

The specific combination of the ingredients in the preparation can be accomplished by way of a novel extraction procedure of curcuminoids from rhizomae of *Curcuma longa*. The curcuminoid combination can be isolated by:

a) drying and powdering tumeric rhizomae to produce a resulting powder,
b) extracting the resulting powder with a solvent at a temperature between 30°–60° C. to produce an extract,
c) concentrating said extract,
d) lowering the temperature of said concentrated extract to between 0°–15° C. to crystallize any curcuminoids present,
e) isolating any resulting crystals,
f) dissolving any isolated crystals of curcuminoids in a solvent at a temperature between 30°–50° C.,
g) lowering the temperature of the dissolved curcuminoids to a temperature between 0°–15° C., and
h) isolating any curcuminoids present.

Examples of suitable solvents used to extract the powder are ethylene dichloride, methylene dichloride and ethyl acetate. The volume of solvent can be 3 to 9 volumes calculated on the dry weight of powdered turmeric rhizomae. The extraction procedure can be repeated several times and the individual extracts combined before concentration. The extracts can be filtered and concentrated by distillation under vacuum at temperatures just under 50° C. Suitable solvents for dissolving the crystals of curcuminoids are $C_1$–$C_6$ alkyl ketone solvents preferably acetone, methyl ketone, etc. Steps d)–g) are critical for obtaining the desired composition of curcuminoids. As a result of this extraction procedure the unique composition of curcuminoids is obtained.

Characteristics of the composition of the invention

Description: orange yellow crystalline powder.

Solubility: slightly soluble in alcohol, soluble in acetone and in glacial acetic acid.

Identification: by UV absorption; by boric acid test—dilute ethanolic solution after acidifying with hydrochloric acid gives a reddish color with boric acid.

Melting range: melts between 180° and 185° C.

Loss on drying: not more than 0.5% w/w.

Assay by HPLC: determines composition of curcuminoids within specified range.

B. The method for complexation of curcuminoids with metals is also a novel procedure. Curcuminoids form complexes with nontoxic metals like calcium, zinc, magnesium, chromium, etc. Curcuminoids can be complexed with metals using the following steps:

a) dissolving at least one curcuminoid in a mixture of methanol and acetone,
b) heating the resulting mixture to 40°–50° C.,
c) preparing a metal solution by dissolving a metal in a solvent,
d) adding the metal solution to the solution of curcuminoid to produce a mixture,
e) adjusting the pH of the mixture to 7.5–9.5 to precipitate any metal complexes,
f) filtering any metal complexes which precipitate, and
g) drying the metal complexes.

An example of the above described process is given hereby for a calcium complex with curcuminoids. As discussed above, the present method is suitable to prepare other metal complexes with curcuminoids.

1. The 36.8 gm of curcuminoids is dissolved in a mixture of methanol and acetone.
2. The mixture is heated to 40°–50° C. for 1–2 hours.
3. Simultaneously, a solution of calcium chloride is prepared by dissolving 5.5 gm of calcium chloride in methanol. The solution is filtered.
4. Calcium chloride solution is added to the solution of curcuminoids and stirred for 2–3 hours.
5. The pH of the mixture is adjusted to 7.5–9.5 using ammonia to precipitate the metal complexes.
6. The precipitate is filtered and washed with water and finally rinsed with methanol.
7. The wet cake is dried at 70°–80° C.
8. The yield is approximately 25 gm of calcium complex with curcuminoids.

The described method of complexation is novel for the following reasons:

the process complexes curcuminoids selectively;
the ratio of solvents used in the process is specific for complete complexation;

the pH of the reaction is specific for quantitative isolation of the complex and stability of the isolated complex;

the purity of the complexed curcuminoids is higher than curcuminoids alone, which may account for more potent biological activity.

The composition of the present invention can be administered alone, or it can be mixed with a pharmaceutically-acceptable carrier or diluent depending on the mode of administration. Oral administration is preferred, but parenteral and topical administration can be used. For oral administration, the composition of this invention can be used in the form of tablets, capsules, granules, powders, lozenges, syrups, elixirs, solutions, suspensions and the like, in accordance with the standard pharmaceutical practice.

For parenteral administration, which includes intramuscular, intraperitoneal, subcutaneous and intravenous use, sterile solutions of the active ingredients are usually prepared, and the pH of the solutions are suitably adjusted and buffered. For intravenous use, the total concentration of solutes should be controlled to render the preparation isotonic.

Carriers useful in formulating the preparations are commonly used pharmaceutically acceptable non-toxic carriers such as gelatin, lactose, sodium citrate, salts of phosphoric acid, starch, magnesium stearate, sodium lauryl sulphate, talc, polyethylene glycol etc. The carrier may be used with other additives such as diluents, binders, buffer agents, preservatives, sweetening agents, flavoring agents, glazes, disintegrators, coating agents, emulsifying agents, suspending agents, etc.

The daily dose of the preparation can be appropriately determined and is not particularly limited. However, in most instances, an effective dosage for an adult will be between 50–500 mg/three times per os.

References

1. Ho, C. T. , Chen, Q., Shi, H., Zhang, K. Q. and Rosen. R. T. (1992) "Antioxidative effect of polyphenol extract prepared from various Chinese tea", *Preventive Med.*, 21:520–525 [RANCIMAT METHOD].

2. Yen, G. C., Duh, P. D. (1994) "Scavenging effect of methanolic extracts of peanut hulls on free-radical and active-oxygen species", *J. Agric. Food Chem.*, 42:629–632 [DPPH RADICAL SCAVENGING].

We claim:

1. A method for neutralizing free radicals and for preventing the formation of free radicals in a patient, comprising administering to a patient in need of such treatment an effective amount of a composition comprising the following components: curcumin, demethoxy curcumin, and bis demethoxy curcumin, wherein said components are purified individually or in combination and adjusted to the following ranges: 75–81% curcumin, 15–19% demethoxy curcumin, and 2.2–6.5% bis demethoxy curcumin.

2. The method according to claim 1, wherein said bis demethoxy curcumin is present in an amount less than 5%.

3. A method for isolating curcuminoids, comprising the following steps:
    a) drying and powdering tumeric rhizomae to produce a resulting powder,
    b) extracting the resulting powder with a solvent at a temperature between 30°–60° C. to produce an extract,
    c) concentrating said extract,
    d) lowering the temperature of said concentrated extract to between 0°–15° C. to crystallize any curcuminoids present,
    e) isolating any resulting crystals,
    f) dissolving any isolated crystals of curcuminoids in a solvent at a temperature between 30°–50° C.,
    g) lowering the temperature of the dissolved curcuminoids to a temperature between 0°–15° C., and
    h) isolating any curcuminoids present.

4. The method according to claim 3, wherein step b) is repeated at least once to produce additional extracts.

5. The method according to claim 3, wherein said extract is filtered before concentration.

6. The method according to claim 3, wherein said extract is concentrated by distillation under vacuum.

7. The method according to claim 3, wherein said crystals of curcuminoids are dissolved in a $C_1$–$C_6$ alkyl ketone solvent.

8. The method according to claim 7, wherein said $C_1$–$C_6$ alkyl ketone solvent is selected from the group consisting of acetone and methyl ketone.

9. The method according to claim 3, wherein said solvent is selected from the group consisting of ethylene dichloride, methylene dichloride and ethyl acetate.

10. A method for complexing curcuminoids with metals comprising the following steps:
    a) dissolving at least one curcuminoid in a mixture of methanol and acetone,
    b) heating the resulting mixture to 40°–50° C. for 1–2 hours,
    c) preparing a metal solution by dissolving a metal in a solvent,
    d) adding the metal solution to the solution of curcuminoid to produce a mixture,
    e) adjusting the pH of the mixture to 7.5–9.5 to precipitate any metal complexes,
    f) filtering any metal complexes which precipitate, and
    g) drying the metal complexes.

11. The method according to claim 10, wherein said solvent is methanol.

12. The method according to claim 10, wherein said pH is adjusted using ammonia.

13. The method according to claim 10, wherein said metal complexes are washed with water and rinsed with methanol after step f).

14. The method according to claim 10, wherein said metal complexes are dried at a temperature between 70°–80° C.

15. The method according to claim 10, wherein said metal is calcium chloride.

16. A method for protecting biological tissues from damage, comprising administering to a patient in need of such treatment an effective amount of a composition comprising the following components: curcumin, demethoxy curcumin, and bis demethoxy curcumin, wherein said components are purified individually or in combination and adjusted to the following ranges: 75–81% curcumin, 15–19% demethoxy curcumin, and 2.2–6.5% bis demethoxy curcumin.

17. An bioprotectant composition, comprising the following components: 75–81% curcumin, 15–19% demethoxy curcumin, and 2.2–6.5% bis demethoxy curcumin, wherein said composition is produced by the following steps:

a) drying and powdering tumeric rhizomae to produce a resulting powder, b) extracting the resulting powder with a solvent at a temperature between 30°–60° C. to produce an extract, c) concentrating said extract, d) lowering the temperature of said concentrated extract to between 0°–15° C. to crystallize any curcuminoids present, e) isolating any resulting crystals, f) dissolving any isolated crystals of curcuminoids in a solvent at a temperature between 30°–50° C., g) lowering the temperature of the dissolved curcuminoids to a temperature between 0°–15° C., and h) isolating any curcuminoids present.

* * * * *